(12) United States Patent
Wheeler et al.

(10) Patent No.: US 11,278,716 B2
(45) Date of Patent: Mar. 22, 2022

(54) ELECTRODE ARRAY FOR SURFACE AND INTRATISSUE RECORDING AND STIMULATION

(71) Applicant: THE CHARLES STARK DRAPER LABORATORY, INC., Cambridge, MA (US)

(72) Inventors: Jesse J. Wheeler, Revere, MA (US); John R. Burns, IV, Boston, MA (US); John Lachapelle, Princeton, MA (US); Caroline K. Bjune, Arlington, MA (US); Philip D. Parks, II, Wayland, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 822 days.

(21) Appl. No.: 15/897,019

(22) Filed: Feb. 14, 2018

(65) Prior Publication Data
US 2018/0229025 A1 Aug. 16, 2018

Related U.S. Application Data

(60) Provisional application No. 62/458,998, filed on Feb. 14, 2017, provisional application No. 62/459,001, filed on Feb. 14, 2017.

(51) Int. Cl.
*A61N 1/05* (2006.01)
*A61N 1/36* (2006.01)
(Continued)

(52) U.S. Cl.
CPC ................ *A61N 1/05* (2013.01); *A61B 5/24* (2021.01); *A61B 5/296* (2021.01); *A61B 5/316* (2021.01);
(Continued)

(58) Field of Classification Search
CPC ........ A61N 1/05; A61N 1/36; A61N 1/36125; A61N 1/36128; A61N 1/365;
(Continued)

(56) References Cited

U.S. PATENT DOCUMENTS 6,141,588 A 10/2000 Cox et al.
7,006,859 B1 * 2/2006 Osorio ................. A61N 1/0539
600/378
(Continued)

FOREIGN PATENT DOCUMENTS

WO 03033070 A1 4/2003

OTHER PUBLICATIONS

International Search Report and Written Opinion for application No. PCT/US2018/018243 dated Jun. 19, 2018.
(Continued)

*Primary Examiner* — Eun Hwa Kim
(74) *Attorney, Agent, or Firm* — Lando & Anastasi, LLP

(57) ABSTRACT

An electrode array includes a body portion, at least one tail portion, at least one tissue surface contact, and at least one intratissue contact. The electrode array can provide stimulation or record signals from both the surface of a target tissue and within the target tissue. A system for tissue surface and intratissue signal recording and/or stimulation contains an electrode array, a controller or receiver, and at least one connection between the electrode array and the controller or receiver. A method of recording signals and/or stimulating tissue includes contacting the target tissue surface and target tissue interior with an electrode array and providing or recording an electrical, chemical, or optical signal.

21 Claims, 4 Drawing Sheets

(51) Int. Cl.
| | |
|---|---|
| *A61B 5/00* | (2006.01) |
| *A61B 5/24* | (2021.01) |
| *A61B 5/296* | (2021.01) |
| *A61B 5/316* | (2021.01) |
| *A61N 1/365* | (2006.01) |
| *A61N 1/372* | (2006.01) |
| *A61N 1/04* | (2006.01) |
| *A61B 5/30* | (2021.01) |

(52) U.S. Cl.
CPC .......... *A61B 5/6847* (2013.01); *A61B 5/6877* (2013.01); *A61N 1/36* (2013.01); *A61N 1/365* (2013.01); *A61N 1/3606* (2013.01); *A61N 1/36125* (2013.01); *A61N 1/36128* (2013.01); *A61N 1/37211* (2013.01); *A61B 5/30* (2021.01); *A61B 2562/028* (2013.01); *A61B 2562/04* (2013.01); *A61B 2562/125* (2013.01); *A61N 1/0404* (2013.01); *A61N 1/0502* (2013.01); *A61N 1/0504* (2013.01); *A61N 1/36003* (2013.01); *A61N 1/36062* (2017.08); *A61N 1/36114* (2013.01)

(58) Field of Classification Search
CPC .............. A61N 1/37211; A61N 1/3606; A61N 1/0502; A61N 1/36003; A61N 1/0504; A61N 1/0404; A61N 1/36062; A61N 1/36114; A61B 2562/028; A61B 2562/04; A61B 2562/125; A61B 5/24; A61B 5/296; A61B 5/316; A61B 5/6877; A61B 5/6847; A61B 5/30
See application file for complete search history.

(56) References Cited

U.S. PATENT DOCUMENTS

| | | |
|---|---|---|
| 2008/0154328 A1 | 6/2008 | Thompson et al. |
| 2009/0118804 A1 | 5/2009 | Moffitt et al. |
| 2012/0277834 A1* | 11/2012 | Mercanzini ............ A61B 5/291 607/62 |
| 2013/0289683 A1 | 10/2013 | Parker et al. |
| 2014/0343621 A1 | 11/2014 | Decre et al. |
| 2016/0015979 A1 | 1/2016 | McLaughlin et al. |
| 2016/0074655 A1 | 3/2016 | Mercanzini et al. |
| 2016/0270679 A1 | 9/2016 | Mahon et al. |
| 2016/0331973 A1 | 11/2016 | Wheeler et al. |
| 2017/0225447 A1 | 8/2017 | Varadan et al. |

OTHER PUBLICATIONS

International Search Report and Written Opinion for application No. PCT/US2018/018244 dated Apr. 26, 2018.

Invitation to Pay Additional Fees and Partial International Search Report for application No. PCT/US2018/018243 dated Apr. 25, 2018.

\* cited by examiner

ELECTRODE ARRAY FOR SURFACE AND INTRATISSUE RECORDING AND STIMULATION

CROSS-REFERENCE TO RELATED APPLICATIONS

This application claims priority under 35 U.S.C. § 119(e) to U.S. Provisional Application No. 62/458,998 titled "ELECTRODE ARRAY FOR SURFACE AND INTRATISSUE RECORDING AND STIMULATION," filed Feb. 14, 2017, and U.S. Provisional Application No. 62/459,001 titled "LEAD ASSEMBLY FOR NETWORKED IMPLANTS," filed Feb. 14, 2017, which are incorporated herein by reference in their entireties for all purposes.

FIELD OF TECHNOLOGY

Aspects and embodiments disclosed herein relate to systems and methods for surface and intratissue signal recording and stimulation. In particular, aspects and embodiments disclosed herein relate to electrode arrays containing multiple contacts disposed both on the surface of a target tissue and within the target tissue.

SUMMARY

In accordance with an aspect, there is provided an electrode array capable of providing stimulation or recording signals from a target tissue. The electrode array may comprise a body portion configured to contact a surface of the target tissue. The electrode array may comprise at least one tail portion extending from the body portion, configured to be inserted within the target tissue. The electrode array may further comprise at least one tissue surface contact and at least one intratissue contact. The at least one tissue surface contact may be disposed on the body portion of the electrode array and configured to provide stimulation or record signals from the target tissue surface. The at least one intratissue contact may be disposed on each of the at least one tail portion of the electrode array and configured to provide stimulation or record signals from within the target tissue.

In some embodiments, the stimulation or signals may comprise electrical, chemical, or optical signals.

The electrode array may further comprise an antenna electrically connected to the at least one tissue surface contact or to the at least one intratissue contact. In some embodiments, the antenna may be electrically connectable to an implanted controller or receiver.

The electrode array may further comprise at least one connection tab adjacent or within the body portion.

In some embodiments, at least one of the body portion and the at least one tail portion is structured to at least partially conform to the target tissue. In some embodiments, at least one of the body portion and the at least one tail portion comprises a support structure. The support structure may be reversibly removable.

In some embodiments, the at least one tissue surface contact is positioned to face the target tissue. In some embodiments, the at least one tissue surface contact is positioned to face away from the target tissue.

In accordance with another aspect, there is provided a system for providing stimulation or recording signals from a target tissue. The system may comprise an electrode array comprising at least one tissue surface contact and at least one intratissue contact. The at least one tissue surface contact may be disposed on a body portion. The at least one intratissue contact may be disposed on a tail portion extending from the body portion.

The system may comprise a controller or receiver connected to the electrode array and configured to provide or receive signals from the electrode array. The system may comprise at least one connection between the electrode array and the controller or receiver. One or more components of the system may be connected wirelessly or through one or more lead wires.

In some embodiments, the at least one connection comprises a lead line. In some embodiments, the at least one connection comprises an antenna.

The controller or receiver may further be configured to record the signals. The stimulation or signals may comprise electrical, chemical, or optical signals.

In some embodiments, the system comprises a plurality of electrode arrays. Each of the electrode arrays may be connectable to the controller or receiver. Each of the electrode arrays may be inter-connectable.

In accordance with another aspect, there is provided a method for providing stimulation or recording signals from a target tissue. The method may comprise contacting the target tissue with an electrode array. The electrode array may comprise at least one tissue surface contact configured to contact a target tissue surface. The electrode array may comprise at least one intratissue contact configured to contact a target tissue interior. The at least one tissue surface contact and the at least one intratissue contact may be disposed on a single assembly.

The method may comprise providing electrical, chemical, or optical stimulation to the target tissue surface and the target tissue interior through the electrode array. The method may comprise obtaining at least one electrical, chemical, or optical signal from the target tissue surface and the target tissue interior through the electrode array.

In some embodiments, the method may further comprise transmitting the electrical, chemical, or optical stimulation from a controller to the electrode array. The method may further comprise transmitting the electrical, chemical, or optical signal to a receiver. The method may further comprise recording the electrical, chemical, or optical signal on the receiver.

In some embodiments, contacting the target tissue comprises implanting a portion of the assembly comprising the at least one intratissue contact into the target tissue. The portion of the assembly implanted into the target tissue may comprise a support structure. The method may further comprise removing the support structure after implanting the portion of the assembly.

In some embodiments, obtaining at least one signal from the target tissue surface comprises obtaining a signal from an environment surrounding the target tissue. The method may further comprise referencing the signal from the environment surrounding the target tissue to the signal from the target tissue interior.

The disclosure contemplates all combinations of any one or more of the foregoing aspects and/or embodiments, as well as combinations with any one or more of the embodiments set forth in the detailed description and any examples.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
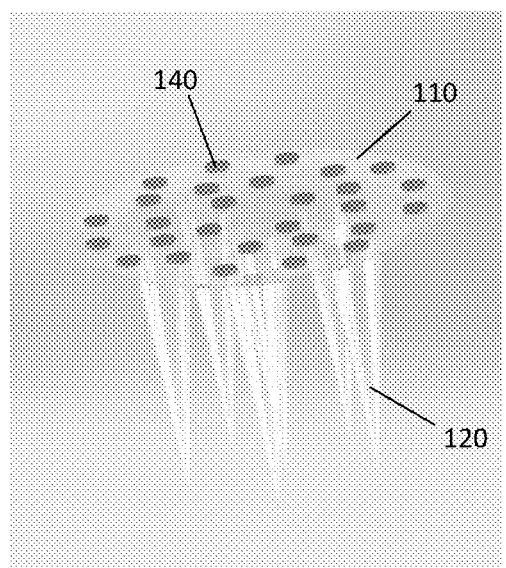
FIG. 1 is a schematic diagram of an electrode array, according to one embodiment.

Skeletal muscle comprises blood vessels, connective tissue, and muscle fibers. The muscle fibers in the tissue are organized into muscle fascicles and surrounded by a layer of connective tissue. The connective tissue layer surrounding the fascicles is perimysium, while the connective tissue within the fascicles is endomysium. An additional layer of connective tissue, the epimysium, surrounds blood vessels and muscle fascicles. The epimysium is the surface layer of the muscle.

Electromyography (EMG) is a diagnostic procedure used to assess the muscle tissues and the related nerve tissues that control them (motor neurons). EMG devices may provide electrical stimulation to muscles or nerves and/or record muscle and nerve tissue activity. EMG devices generally include an electrode that contacts the muscle or nerve tissue. Certain EMG devices may include electrodes that contact the external epidermal layer and transmit signals to and from the muscle or nerve tissue through the epidermal layers. Certain other EMG devices may include electrodes that are implanted within the epidermal layer and contact the muscle or nerve tissue surface, for instance the epimysium. Yet other EMG devices may include electrodes that are disposed within the muscle or nerve tissue and contact the internal tissue, for example, the muscle fascicles, perimysium, or the muscle fibers directly.

Systems and methods disclosed herein may be capable of recording and/or stimulating a target tissue by transmitting or receiving signals from the target tissue surface and within the target tissue, simultaneously. The electrode array disclosed herein may provide the ability for clinicians to record and stimulate muscle, bone, nerve, and/or other organ tissue both on the surface of the target tissue and within the target tissue. A single electrode array with surface and intratissue contacts may reduce the need for multiple electrode devices and implants, potentially easing the surgical procedure. Furthermore, a single electrode array with surface and intratissue contacts may reduce the need for complex physical and electrical connections between multiple implantable devices.

In accordance with certain embodiments, systems and methods disclosed herein may be capable of recording and stimulating epimysial tissue and muscle fascicles with a single electrode array. In accordance with other embodiments, systems and methods disclosed herein may be capable of recording and stimulating the cortex and within the brain with a single electrode array. In accordance with other embodiments, systems and methods disclosed herein may be capable of recording and stimulating bone surface and bone marrow with a single electrode array. In accordance with yet other embodiments, systems and methods disclosed herein may be capable of recording and stimulating skeletal and surrounding nerve tissue with a single electrode array. The use of systems and methods disclosed herein is not limited to these embodiments, but may be applied to any target tissue, including, for example, epidermal, muscle, bone, nerve, or organ tissue.

The systems and methods disclosed herein may be used in a number of clinical applications. For instance, the systems and methods are useful in chronic and acute applications. Chronic applications that may benefit from the systems and methods disclosed herein include chronic muscle tissue recovery, cardiac muscle stimulation, neurological stimulation or recording, prosthetic control and monitoring, and skeletal tissue and related nerve monitoring for research and/or application. Acute applications that may benefit from the systems and methods disclosed herein include intraoperative recording, monitoring, and stimulation, and acute muscle tissue recovery.

In accordance with an aspect, there is provided an electrode array comprising at least one tissue surface contact and at least one intratissue contact. The tissue surface contact and intratissue contact may each be arranged according to a predetermined configuration. For instance, more than one surface or intratissue contacts may be arranged in a row, in a grid, in an array, or in a hexagonal pattern. In some embodiments, the tissue surface contact and the at least one intratissue contact are disposed on a single assembly. The single assembly may be enclosed in or comprise a housing, for example, of biocompatible material. In such embodiments where the single assembly comprises a housing, openings may be provided for the tissue contacts. The housing may be hermetically sealed to the assembly.

The tissue surface contact and intratissue contact may be configured to provide stimulation or record signals from the target tissue. In particular, the tissue surface contact may be configured to interface with a surface of the target tissue, while the intratissue contact may be configured to interface with an interior portion of the target tissue. In some embodiment, the tissue surface contact or intratissue contact may comprise an electrode. The tissue surface contact or intratissue contact may comprise a sensor, for example, configured to measure chemical or optical signals. The tissue surface contact or intratissue contact may comprise a fluid delivery point. The tissue surface contact or intratissue contact may comprise a light source.

In certain configurations, the tissue surface contact may face the tissue surface and interface with the target tissue. In some embodiments, the tissue surface contact may face away from the tissue. The tissue surface contact may be configured to record signals from the environment surrounding the tissue. The signals recorded or transmitted by the intratissue contact may be referenced to the tissue surface signals. The environment surrounding the tissue may be the environment in the vicinity of the tissue or in the immediate vicinity of the tissue. For example, the environment may include a body cavity, body fluids, or adjacent tissues and organs.

In some embodiments, the surface tissue may be epimysial tissue, peripheral nerve tissue, cortex tissue, bone tissue, or surface cardiac tissue. In some embodiments, the intratissue may comprise perimyseum, endomysium, muscle fiber, muscle fascicle, cardiac tissue, brain tissue, bone tissue, bone marrow, neural tissue, or nerve tissue. For example, the electrode array may comprise at least one epimysial contact and at least one intramuscular contact.

The electrode array may comprise a body portion, a tail portion, and a connection tab. The body portion may be provided to contact a surface of the target tissue. The tail portion may be provided to be inserted within the target tissue. The connection tab may be provided to anchor the electrode array to the tissue. In one embodiment, the connection tab is disposed adjacent to or within the body portion. The connection tab may comprise a clamp mechanism or suture point for connecting the electrode array to the tissue surface.

The tail portion and body portion may be connected to each other in any regular or irregular configuration. In one embodiment, the tail portion and body portion are connected to each other in a T shaped configuration. In other examples, the tail portion and body portion may be connected to each other in an L, Y, or I shaped configuration. The tail portion and body portion may be connected to each other in an umbrella shaped configuration. The electrode array may comprise more than one tail portion extending from or branching out of the body portion. The more than one tail portion may be connected to the body portion in a table or star shaped configuration. In an alternate configuration, the electrode array may comprise more than one body portion connected to a singular tail portion. In some embodiments, the electrode array may comprise more than one body portion and more than one tail portion. According to certain embodiments, the body portion is a frame or cuff, dimensioned larger than the tail portion. The body portion may comprise macro contacts while the tail portion comprises micro contacts. According to certain embodiments, the tail portion is elongated. The body and tail portion may be arranged such that the body is adjacent to the outer tissue and the tail penetrates into the tissue.

As disclosed herein, "electrode array" refers to a system of interconnected electrode contacts that are connected or connectable to a central controller or receiver. The electrodes may be connected or connectable through a singular connection. The singular connection may be, for example, wireless, through one or two common wires, or through a bundled set of wires. In certain embodiments, the electrode array is of biocompatible material, flexible, and secured. The electrode array may comprise non-corrosive conductors in high electrical isolation from each other.

The electrode array may comprise laser cut, thin film components. For instance, the thin film components may comprise platinum, gold, or another suitable metal. The components may be embedded in a polymer, for example polydimethylsiloxane (PDMS). The components may be embedded in any other suitable biocompatible polymer. The electrical array may be reinforced by a fine mesh. The fine mesh may provide mechanical support. The fine mesh may be less than about 1 mm thick, for example it may be about 0.5 mm thick.

The electrode array may be structured to at least partially conform to the surface of the target tissue. In some embodiments, at least one of the body portion and the tail portion is structured to at least partially conform to the target tissue. The electrode array may comprise a flexible material selected to correlate to the target tissue. For example, properties of the flexible material may correlate to mechanical properties of the target tissue, such that the electrode array conforms to the surface and interior of the target tissue during movement.

The electrode array may comprise a support structure. In some embodiments, at least one of the body portion and the at tail portion may comprise a support structure. The support structure may comprise a rigid material for reinforcement. The rigid material may enable insertion or removal of the electrode array from the target tissue. For instance, the support structure may be provided on the electrode array at the point of insertion into the target tissue. In general, the stiffness of the support structure may be selected to correlate with the target tissue. For instance, an electrode array for use with bone may require a support structure with greater rigidity than an electrode array for use with nerve tissue. The support structure may generally have greater rigidity and/or stiffness than the target tissue, allowing manual or mechanical insertion into the tissue.

In some embodiments, the support structure may be reversibly removable from the electrode array. The support structure may be a mechanical backing or lead. The support structure may comprise a needle or stylet. Methods for attaching the electrode array to target tissue may include implanting the portion of the electrode array with the support structure into the target tissue, followed by removal of the support structure. Similarly, methods for removal of the electrode array from target tissue may include attaching the support structure to the electrode array and removing both from the target tissue. Insertion, implantation, or removal of the electrode array may be performed surgically. Insertion, implantation, or removal of the electrode array may be performed manually or mechanically.

The electrode array may be dimensioned to correspond to the target tissue. For instance, an electrode array configured to correspond to skeletal muscle may be larger than an electrode array configured to correspond to nerve tissue. Accordingly, the electrode array may be dimensioned between about several millimeters (mm), for example 10 mm, 5 mm, or less than 1 mm, and about several centimeters (cm), for example 1 cm, 5 cm, up to about 10 cm. In one embodiment, the electrode array comprises a tail portion that is about 5-7 mm in diameter. In another embodiment, the electrode array comprises a tail portion that is about less than one mm in diameter. In some embodiments, the tissue surface contacts are dimensioned on the macro scale. For example, the tissue surface contacts may comprise a one or less than one millimeter diameter. In some embodiments, the intratissue contact may be dimensioned on the micro scale. For example, the intratissue contacts may comprise a diameter that is several micrometers ($\mu m$) long, 10 $\mu m$, 50 $\mu m$, or 100 $\mu m$ long.

In some embodiments, the electrode array is configured to provide stimulation to the target tissue surface and within the target tissue. In some embodiments, the signal may be electrical, chemical, or optical. The stimulation may be provided as an electrical pulse or signal. The electrical pulse or signal may comprise a low frequency current. In some embodiments, the electrical pulse or signal may comprise a high frequency burst. The electrical signal may be provided in regular pulses or as needed. The pulses may last from a few seconds to a few minutes or hours. In some embodiments, the electrical signal is a constant current.

The signal may be provided in a microfluid configured to deliver a chemical signal or drug. The chemical signal or drug may be delivered over an extended period of time, for example lasting several minutes, hours, or days. The chemical signal or drug may be delivered in immediate release intervals. The intervals may be regular or as needed.

The signal may be an optical signal, for example, comprising ultraviolet light or x-rays. The optical signal may be constant or intermittent. The optical signal may be provided in a regular interval or as needed. In some embodiments, the electrode array may be configured to provide more than one type of signal to the target tissue.

In some embodiments, the electrode array is configured to receive signals from the target tissue surface and within the target tissue. The signals may be electrical, chemical, or optical. The electrode array may be configured to detect and record chemical signals, for example concentration of a chemical molecule or drug within the target tissue. The electrode array may be configured to detect and record electrical signals, for example for energy harvesting from the target tissue or monitoring of electrical signals. The electrode array may be configured to detect and record optical signals, for example, for visualization of the target tissue. The signals may be relayed to a controller or receiver and recorded for subsequent or concurrent analysis. In some embodiments, the signal is displayed on a display device.

In accordance with another aspect, there is provided a system for tissue surface and intratissue signal recording and/or stimulation. The system may comprise an electrode array comprising at least one tissue surface contact and at least one intratissue contact, as previously described. The system may comprise a controller or receiver connected to the electrode array and configured to provide or receive signals from the electrode array. The controller or receiver may be electrically connectable to the electrode array. By electrically connectable, it is meant that in use the controller or receiver is electrically connected to the electrode array. The controller or receiver may be implanted, for example subcutaneously implanted, or external. The controller or receiver may be remote from the electrode array or provided on a single assembly with the electrode array. The controller or receiver may be configured to record the received signals, for example, for analysis or feedback control.

In some embodiments, the electrode array may comprise an antenna. The antenna may be connected to the at least one tissue surface contact or to the at least one intratissue contact. In some embodiments, the antenna may be electrically connected to the controller or receiver. For example, the antenna may be electrically connected to an implanted controller or receiver. The antenna may enable the electrode array to receive and/or transmit wireless signals to the tissue contacts or the controller or receiver.

The system may further comprise at least one connection between the electrode array and the controller or receiver. The at least one connection may comprise a lead line configured to deliver signals between the electrode array and the controller or receiver. The lead line may comprise a wire or a bundle of wires capable of transmitting data or power. The at least one connection may comprise an antenna. The at least one connection may comprise a plurality of antennas, for example a first antenna associated with the controller or receiver and a second antenna associated with the electrode array. The antenna may be configured to transmit data or power between the electrode array and the controller or receiver. For example, the antenna may be configured to wirelessly transmit data or power.

In some embodiments, the system may comprise a plurality of electrode arrays. Each of the electrode arrays may be electrically connected to another electrode array. For instance, the electrode arrays may be inter-connected. In some embodiments, each of the electrode arrays may be connectable to the controller or receiver. The plurality of electrode arrays may be connected to the controller or receiver in series or in parallel. In some embodiments, the controller or receiver may interface with one or more of the plurality of electrode arrays selectively. For example, one or more of the plurality of electrode arrays may be configured to transmit stimulation to the target tissue, while one or more of the plurality of electrode arrays may be configured to obtain or record signals from the target tissue. One or more components of the system may be connected wirelessly or through one or more lead wires.

The controller or receiver may comprise a main hub module electrically connectable to the electrode array. The controller or receiver may comprise an external base station electrically connected to the main hub module and/or the electrode array.

Systems and methods disclosed herein may further be configured to control stimulation or delivery of a signal based on a recording or measurement of the signal or based on a predetermined schedule.

In accordance with some embodiments, the main hub module provides one or more of power, processing, and system control to one or more electrode arrays. The main hub module may provide electrical pulse or signals to be delivered to the target tissue surface or within the tissue through the electrode array and electrode contacts. The main hub module may also or alternatively be configured to receive and/or record signals received from the electrode array. According to some embodiments, the main hub module is implantable. According to other, alternate embodiments, the main hub module is external. According to some embodiments, the main hub module is connected to a power source or comprises a power source, for example batteries.

In accordance with some embodiments, the external base station comprises a display screen and/or a power switch. The external base station may provide one or more of power, processing, and system control to the main hub module and/or to one or more electrode arrays directly. The external base station may be configured to provide electrical pulse or signals to the main hub or electrode array. Additionally or alternatively, the external base station may be configured to receive, record, and/or display signals received from the main hub or electrode array for future or concurrent analysis. According to some embodiments, the external base station is a power source that provides power to the main hub. According to other embodiments, the external base station is connected to a power source or comprises a power source, for example batteries.

In accordance with another aspect, there is provided a method of recording signals and/or stimulating tissue comprising contacting the target tissue surface and target tissue interior with an electrode array, as previously described. The method may comprise contacting the target tissue with an electrode array comprising at least one tissue surface contact configured to contact a target tissue surface and at least one intratissue contact configured to contact the target tissue interior. The method may further comprise providing an electrical, chemical, or optical stimulation to the electrode array or recording an electrical, chemical, or optical signal through the electrode array.

In some embodiments, an electrical, chemical, or optical signal is transmitted from the electrode array to the controller or receiver. The controller or receiver may further record or display the electrical, chemical, or optical signal.

The method may further comprise analyzing a recorded signal and determining whether to provide a stimulation in response to the analysis of the recorded signal. In some embodiments, the method comprises determining the degree and kind of stimulation to be provided in response to the analysis of the recorded signal.

Intratissue signals may be referenced to surface signals as a reference or ground. In some embodiments, obtaining at least one signal from the target tissue surface comprises obtaining a signal from environment surrounding the target tissue. The method may further comprise referencing the signal from the environment surrounding the target tissue to the signal from the target tissue interior.

The method may comprise transmitting the electrical, chemical, or optical signal between the controller or receiver and the electrode array. The signal may be transmitted to the tissue contacts, which in turn may stimulate the target tissue. In certain embodiments, providing a stimulation includes providing microfluidics comprising a chemical molecule or drug. In other embodiments, providing a stimulation includes providing an electrical signal, for example an electrical current or pulse. In other embodiments, providing a stimulation includes providing ultraviolet light or x-rays. In certain embodiments, more than one stimulation may be provided simultaneously or in turn.

The function and advantages of the embodiments discussed above and other embodiments of the invention can be further understood from the description of the figures below, which further illustrate the benefits and/or advantages of the one or more systems and techniques of the invention but do not exemplify the full scope of the invention.

As shown in FIG. 1, the electrode array may comprise a body portion 110 and a plurality of tail portions 120. A plurality of tissue surface contacts 140 may be positioned away from the extending tail portions 120.

Figure 2:
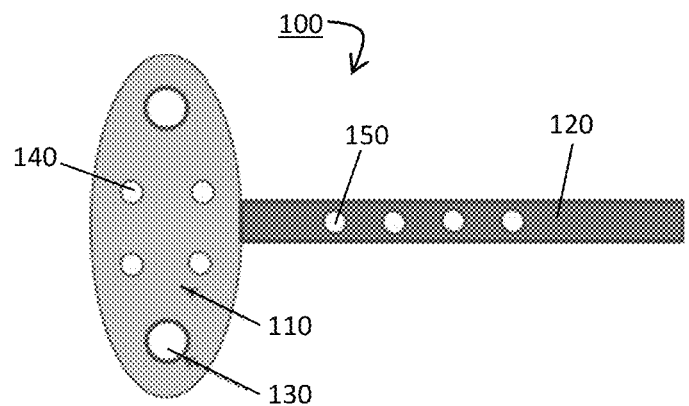
FIG. 2 is a schematic diagram of an electrode array, according to an alternate embodiment.
Figure 3:
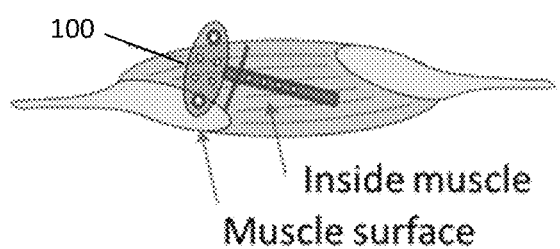
FIG. 3 is diagram showing the schematic electrode array of FIG. 2 in relation to muscle tissue.

As shown in FIG. 2, the electrode array comprises at least one epimysial contact 140 and at least one intramuscular contact 150. The electrode array 100 comprises a body portion 110 comprising the at least one epimysial contact 140, a tail portion 120 comprising the at least one intramuscular contact 150, and a connection tab 130. As shown in FIG. 3, the body portion 110 of the electrode array 100 may remain on the surface of the muscle, and the tail portion 120 of the electrode array 100 may be implanted within the muscle.

Figure 4:
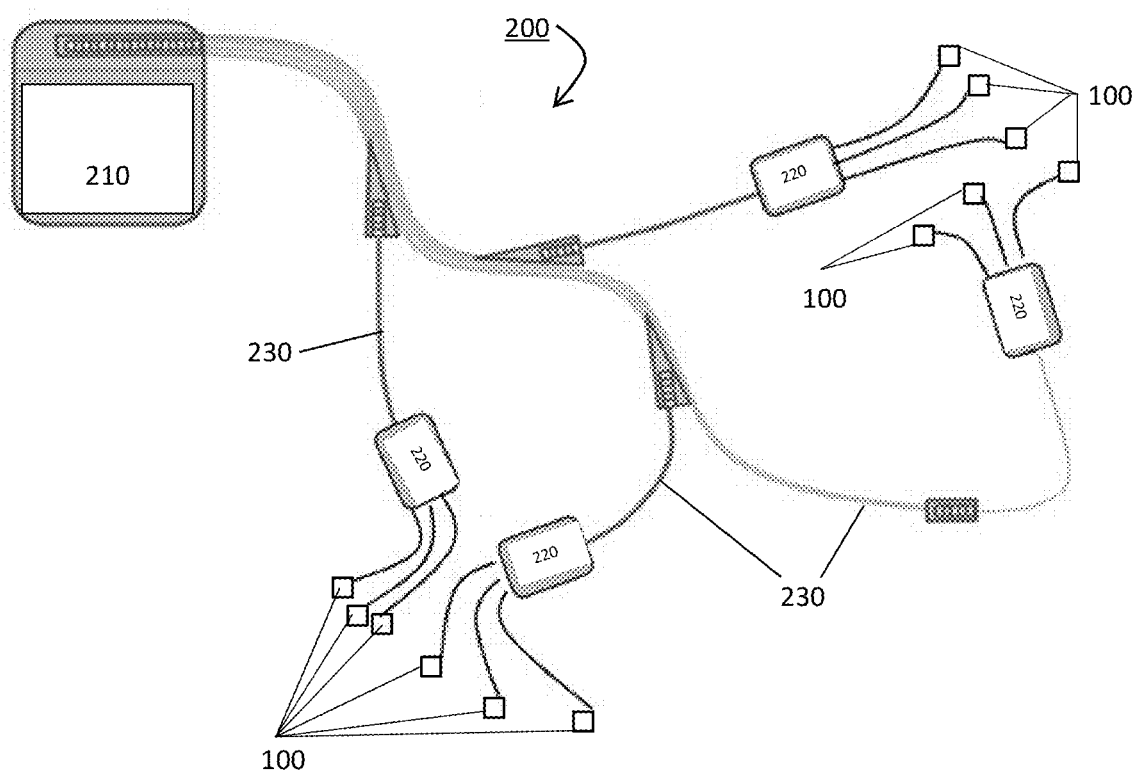
FIG. 4 is a schematic diagram of a system for tissue recording and stimulation, according to one embodiment.

With particular reference to FIG. 4, the system 200 for providing stimulation or recording electrical signals from a target tissue may comprise an electrode array 100, a controller or receiver connected to the electrode array, shown in the figure as a main hub module 220 and an external base station 210, and at least one lead line 230.

Figure 5:
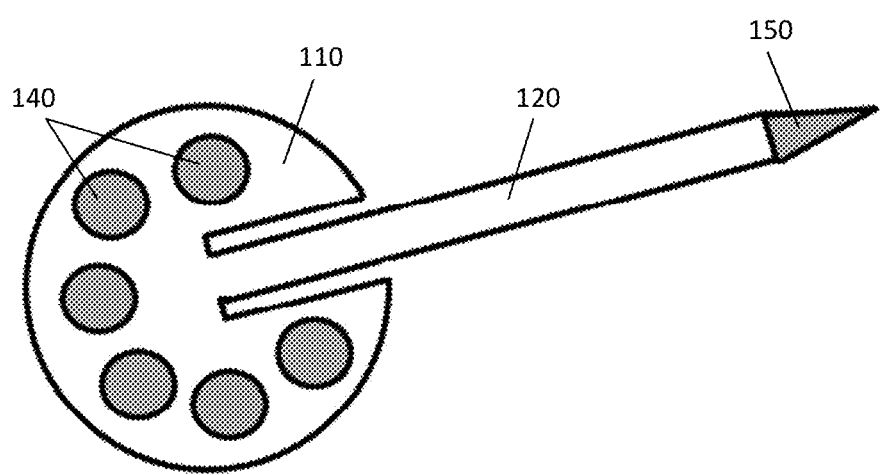
FIG. 5 is a schematic diagram of an electrode array, according to an alternate embodiment.

As shown in FIG. 5, the electrode array may comprise a body portion 110 and a tail portion 120. The body portion 110 may be flexible such that the tissue surface contacts 140 may be positioned to face the tissue surface or away from the tissue surface. The tail portion 120 may be rigid such that it is insertable in the tissue. The tail portion 120 may comprise an intratissue contact 150.

Those skilled in the art should appreciate that the parameters and configurations described herein are exemplary and that actual parameters and/or configurations will depend on the specific application in which the disclosed methods and materials are used. Those skilled in the art should also recognize or be able to ascertain, using no more than routine experimentation, equivalents to the specific embodiments disclosed. For example, those skilled in the art may recognize that the method, and components thereof, according to the present disclosure may further comprise a network or systems or be a component of a system for recording and stimulation of surface tissue and within the tissue. It is therefore to be understood that the embodiments described herein are presented by way of example only and that, within the scope of the appended claims and equivalents thereto; the disclosed embodiments may be practiced otherwise than as specifically described. The present systems and methods are directed to each individual feature, system, or method described herein. In addition, any combination of two or more such features, systems, or methods, if such features, systems, or methods are not mutually inconsistent, is included within the scope of the present disclosure. The steps of the methods disclosed herein may be performed in the order illustrated or in alternate orders and the methods may include additional or alternative acts or may be performed with one or more of the illustrated acts omitted.

Further, it is to be appreciated that various alterations, modifications, and improvements will readily occur to those skilled in the art. Such alterations, modifications, and improvements are intended to be part of this disclosure, and are intended to be within the spirit and scope of the disclosure. In other instances, an existing facility may be modified to utilize or incorporate any one or more aspects of the methods and systems described herein. Thus, in some instances, the systems may involve an electrode array capable of recording and stimulating target tissue surface and within the target tissue. Accordingly the foregoing description and figures are by way of example only. Further the depictions in the figures do not limit the disclosures to the particularly illustrated representations.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

While exemplary embodiments of the disclosure have been disclosed, many modifications, additions, and deletions may be made therein without departing from the spirit and scope of the disclosure and its equivalents, as set forth in the following claims.

What is claimed is:

1. An electrode array capable of providing stimulation or recording signals from a target tissue, the electrode array comprising:
   a body portion comprising an upper surface and a bottom surface, wherein the bottom surface is configured to contact a surface of the target tissue;
   at least one tail portion extending from the body portion, configured to be inserted within the target tissue;
   at least one tissue surface contact disposed on the upper surface of the body portion of the electrode array, positioned to face away from the target tissue and configured to provide stimulation or record signals from the target tissue surface; and
   at least one intratissue contact disposed on each of the at least one tail portion of the electrode array, configured to provide stimulation or record signals from within the target tissue.

2. The electrode array of claim 1, wherein the stimulation or signals comprise electrical, chemical, or optical signals.

3. The electrode array of claim 1, further comprising an antenna connected to the at least one tissue surface contact or to the at least one intratissue contact.

4. The electrode array of claim 3, wherein the antenna is electrically connectable to an implanted controller or receiver.

5. The electrode array of claim 1, further comprising at least one connection tab adjacent to or within the body portion.

6. The electrode array of claim 1, wherein the body portion is formed from a flexible material configured to conform to the target tissue during movement and wherein at least one of the body portion and the at least one tail portion is structured to at least partially conform to the target tissue.

7. The electrode array of claim 6, wherein at least one of the body portion and the at least one tail portion comprises a support structure coupled to the flexible material.

8. The electrode array of claim 7, wherein the support structure is reversibly removable from the flexible material in use.

9. The electrode array of claim 1, further comprising at least one tissue surface contact disposed on the bottom surface of the body portion positioned to face the target tissue.

10. A system for providing stimulation or recording signals from a target tissue, the system comprising:
   a plurality of electrode arrays, each electrode array comprising:
      a body portion comprising an upper surface and a bottom surface, the bottom surface being configured to contact a surface of the target tissue,
      at least one tissue surface contact disposed on the upper surface of a body portion positioned to face away from the target tissue and configured to provide stimulation or record signals from the target tissue surface, and
      at least one intratissue contact disposed on a tail portion extending from the body portion;
   a controller or receiver connectable to each of the plurality of electrode arrays and configured to provide or receive signals from the plurality of electrode arrays; and
   at least one connection between the plurality of electrode arrays and the controller or receiver.

11. The system of claim 10, wherein the at least one connection comprises a lead line.

12. The system of claim 10, wherein the at least connection comprises an antenna.

13. The system of claim 10, wherein the controller or receiver is further configured to record the signals.

14. The system of claim 10, wherein the stimulation or signals comprise electrical, chemical, or optical signals.

15. The system of claim 10, wherein the body portion of each electrode array is formed from a flexible material configured to conform to the target tissue during movement and wherein at least one of the body portion and the at least one tail portion is structured to at least partially conform to the target tissue.

16. The system of claim 15, wherein at least one of the body portion and the at least one tail portion comprises a support structure coupled to the flexible material.

17. The system of claim 16, wherein the support structure is reversibly removable from the flexible material in use.

18. The system of claim 10, wherein each of the electrode arrays further comprises at least one tissue surface contact disposed on the bottom surface of the body portion and positioned to face the target tissue.

19. The system of claim 10, wherein the controller or receiver is configured to selectively provide or receive signals from the plurality of electrode arrays.

20. The system of claim 19, wherein the controller or receiver is configured to direct the one or more of the plurality of electrode arrays to transmit stimulation to the target tissue and one or more of the plurality of electrode arrays to obtain signals from the target tissue simultaneously.

21. The system of claim 14, wherein the controller or receiver is configured to provide more than one type of stimulation or signal selected from the electrical, chemical, or optical signals simultaneously.

* * * * *